United States Patent [19]

Shutske et al.

[11] Patent Number: 5,391,553
[45] Date of Patent: Feb. 21, 1995

[54] SUBSTITUTED 9-AMINO-TETRAHYDROACRIDINES AND RELATED COMPOUNDS

[75] Inventors: Gregory M. Shutske, Somerset; Grover C. Helsley, Pluckemin; Kevin J. Kapples, Little York, all of N.J.

[73] Assignee: Hoechst-Roussel Pharmaceuticals Inc., Somerville, N.J.

[21] Appl. No.: 244,212

[22] Filed: Sep. 14, 1988

Related U.S. Application Data

[63] Continuation-in-part of Ser. No. 26,730, Mar. 17, 1987, abandoned.

[51] Int. Cl.$^6$ .............. C07D 219/10; C07D 221/16; A61K 31/435
[52] U.S. Cl. .................. 514/290; 514/297; 546/79; 546/93; 546/102; 546/103; 546/105
[58] Field of Search ............ 546/79, 93, 102, 103, 546/105, 106; 514/290, 297

[56] References Cited

U.S. PATENT DOCUMENTS

| | | | |
|---|---|---|---|
| 3,232,945 | 2/1966 | Sigal, Jr. et al. | 546/93 |
| 3,318,895 | 5/1967 | Pribyl et al. | 546/93 |
| 3,318,896 | 5/1967 | Pribyl et al. | 546/93 x |
| 3,541,066 | 11/1970 | Wolf | 546/63 |
| 3,580,915 | 5/1971 | Wolf et al. | 546/63 |
| 3,637,706 | 1/1972 | Wolf et al. | 544/361 |
| 3,647,800 | 3/1972 | Wolf et al. | 546/81 |
| 3,657,233 | 4/1972 | Wolf et al. | 544/127 |
| 3,674,790 | 7/1972 | Wolf et al. | 546/81 |
| 3,987,047 | 10/1976 | Griss et al. | 540/580 |
| 4,108,998 | 8/1978 | Demerson et al. | 514/291 |
| 4,631,286 | 12/1986 | Shutske et al. | 514/297 |
| 4,695,573 | 9/1987 | Shutske et al. | 514/290 |
| 4,762,841 | 8/1988 | Shutske | 514/278 |
| 4,816,456 | 3/1989 | Summers | 514/255 |
| 4,851,536 | 7/1989 | Skotnicki et al. | 546/106 |
| 4,985,430 | 1/1991 | Morita et al. | 514/253 |
| 4,999,430 | 3/1991 | Kester et al. | 546/105 |

FOREIGN PATENT DOCUMENTS

| | | |
|---|---|---|
| 0179383 | 4/1986 | European Pat. Off. |
| 0268871 | 6/1988 | European Pat. Off. |
| 1022940 | 3/1966 | United Kingdom ............ 546/79 |

OTHER PUBLICATIONS

Pang, et al., "Drug Absorption, Distribution and Elimination", Burger's Medicinal Chemistry, 4th ed., Part I, Wolff, ed., New York (1980), pp. 55–90.

Lehninger, "Biochemistry", 2nd ed., Worth Publishers, Inc., New York (1975), pp. 304–305.

(List continued on next page.)

*Primary Examiner*—John M. Ford
*Attorney, Agent, or Firm*—Barbara V. Maurer; Tatsuya Ikeda

[57] ABSTRACT

There are disclosed compounds having the formula

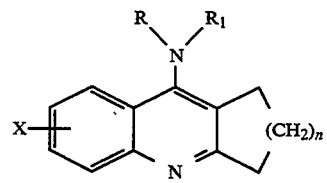

wherein n is 1–4; X is alkyl of 3–18 carbon atoms, cycloalkyl of 3–7 carbon atoms or cycloalkylloweralkyl; R is hydrogen, loweralkyl or loweralkylcarbonyl; $R_1$ is hydrogen, loweralkyl, loweralkylcarbonyl, aryl, diloweralkylaminoloweralkyl, arylloweralkyl, diarylloweralkyl, oxygen-bridged arylloweralkyl or oxygen-bridged diarylloweralkyl; stereo isomers thereof and pharmaceutically acceptable acid addition salts thereof, which are useful for enhancing memory, methods for synthesizing them, and pharmaceutical compositions comprising an effective memory enhancing amount of such a compound.

65 Claims, No Drawings

OTHER PUBLICATIONS

Abramochkin, et al., Khim.-Farm. Zh. (English language version), vol. 4(7), pp. 10–13 (1970).

Konshin, et al. (I), Khim.-Farm. Zh. (English language version), vol. 5(11), pp. 10–12 (1971).

Konshin, et al.(II), Izv. Vyssh. Ucheb. Zaved. Khim. Khim. Tekhnol. (English language version), vol. 15(2), pp. 243–244 (1972).

Konshin, et al.(III), Izv. Vyssh. Ucheb. Zaved. Khim. Khim. Tekhnol. (English language version), vol. 15(5), pp. 726–727 (1972).

Konshin, et al.(IV), Khim. Geterotsikl. Soedin. (English language version), 1973 (No. 4), pp. 531–534.

Konshin, et al.(v), Khim.-Farm. Zh. (English language version), vol. 8(7), pp. 17–19 (1974).

Konshin, Nauch. Tr. Perm. Farmstsevt. Int. (English language version), vol. 10, pp. 6–9 (1976).

Khaldeeva, et al., Khim. Getrotsikl. Soedin. (English language translation) 1976, No. 2, pp. 263–265.

Bialevsky, Coll. Czech. Chem. Commun., vol. 42, pp. 2802–2808 (1977).

Krisna, et al., Ind. J. Chem., vol. 16B(2), pp. 156–158 (1978).

Bun-Hoi, et al., Chemical Abstracts, vol. 69: 106408d (1968).

Patnaik, et al., J. Med. Chem., vol. 9, pp. 483–488 (1966).

Steinberg, et al., J. Med. Chem., vol. 18(11), pp. 1056–1061 (1975).

Ferguson, et al., Chemical Abstracts, vol. 98: 154912j (1983).

Ferguson, et al., Chemical Abstracts, vol. 102: 73854r (1985).

Flood, et al., Chemical Abstracts, vol. 103(7): 48119t (1985).

Cherkin, et al., Chemical Abstracts, vol. 100(5): 114871y (1984).

SUBSTITUTED 9-AMINO-TETRAHYDROACRIDINES AND RELATED COMPOUNDS

This is a continuation-in-part of a prior application, Ser. No. 026,730, filed Mar. 17, 1987, now abandoned.

This invention relates to compounds having the formula

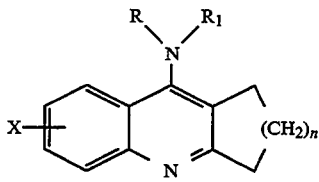

wherein n is 1–4; X is alkyl of 3–18 carbon atoms, cycloalkyl of 3–7 carbon atoms or cycloalkylloweralkyl; R is hydrogen, loweralkyl or loweralkylcarbonyl; $R_1$ is hydrogen, loweralkyl, loweralkylcarbonyl, aryl, diloweralkylaminoloweralkyl, arylloweralkyl, diarylloweralkyl, oxygen-bridged arylloweralkyl or oxygen-bridged diarylloweralkyl; stereo isomers thereof, and pharmaceutically acceptable acid addition salts thereof, which are useful for enhancing memory, methods for synthesizing them, and pharmaceutical compositions comprising an effective memory enhancing amount of such a compound.

This invention also relates to compounds having the formula

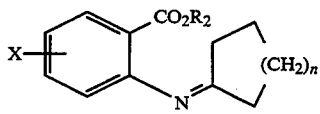

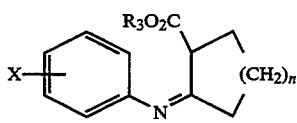

and

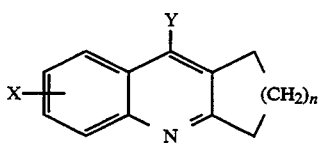

wherein n and X are as defined above, $R_2$ and $R_3$ are hydrogen or loweralkyl, and Y is halogen, hydroxy or loweralkoxy, which are useful as intermediate compounds for synthesizing the compounds of Formula I and methods for synthesizing them.

Throughout the specification and the appended claims, a given chemical formula or name shall encompass all stereo, geometrical and optical isomers thereof where such isomers exist, as well as pharmaceutically acceptable acid addition salts thereof and solvates thereof such as for instance hydrates.

The following definitions shall apply throughout the specification and the appended claims.

Unless otherwise stated or indicated, the term alkyl denotes a straight or branched alkyl group having from 3 to 18 carbon atoms. Examples of said alkyl include n-propyl, iso-butyl, heptyl, decyl, dodecyl, hexadecyl and octadecyl.

Unless otherwise stated or indicated, the term loweralkyl denotes a straight or branched alkyl group having from 1 to 6 carbon atoms. Examples of said loweralkyl include methyl, ethyl, n-propyl, iso-butyl, pentyl and hexyl.

Unless otherwise stated or indicated, the term cycloalkyl denotes a saturated ring containing 3 to 7 carbon atoms. Examples of said cycloalkyl include cyclopropyl, cyclohexyl and cycloheptyl.

Unless otherwise stated or indicated, the term halogen shall mean fluorine, chlorine, bromine or iodine.

Unless otherwise stated or indicated, the term aryl shall mean an unsubstituted phenyl group or phenyl group substituted with 1, 2 or 3 substituents each of which being independently loweralkyl, loweralkoxy, halogen, hydroxy, trifluoromethyl, phenoxy or benzyloxy.

Unless otherwise stated or indicated, the term oxygen-bridged shall signify the fact that an oxygen atom is present between aryl and loweralkyl groups and/or an oxygen atom has replaced a methylene group in the loweralkyl group, with the proviso that said methylene group is not alpha to the amino nitrogen carrying the groups R and $R_1$. Thus, for instance, examples of oxygen-bridged arylloweralkyl include 3-phenoxypropyl and 4-phenoxybutyl, and examples of oxygen-bridged diarylloweralkyl include 2-[bis(4-fluorophenyl)methoxy]ethyl and 2-[bis(3-fluorophenyl)methoxy]ethyl.

The compounds of this invention are prepared by utilizing one or more of the steps described below.

In order to simplify the description of the synthetic schemes, the description will be presented with specific reference to the situation where the group x is cyclohexyl and occupies a specific position in the benzene ring, but it will readily be understood that the synthetic schemes can also be applied to the other situations by making obvious modifications. The substituted anthranilic ester of formula V and its analogues where the group X is other than cyclohexyl, which are used as starting materials, are readily synthesized from the appropriate substituted anilines using conventional techniques well known in the art, such as described by Fuhrer and Gschwend, J. Org. Chem. 44, 1133 (1979) or LaMahieu et al., J. Med. Chem. 26,420 (1983).

Throughout the description of the synthetic steps, the definitions of n, R and $R_1$ are as given above unless otherwise stated or indicated.

STEP A

A compound of Formula IIa can be prepared by reacting compound V, namely, methyl-5-cyclopropyl-2-aminobenzoate, with a cycloalkanone of formula VI. Said reaction can be conducted in a suitable solvent such as benzene, toluene or xylene at a temperature of about 80°–150° C. in the presence of an acid catalyst such p-toluene sulfonic acid, benzenesulfonic acid or methanesulfonic acid.

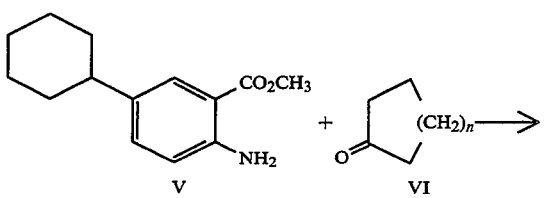
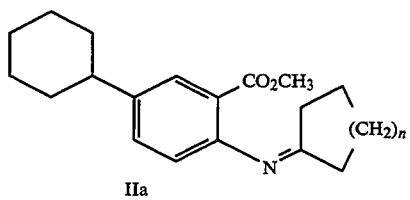

STEP B

A compound of Formula IIIa can be prepared in a manner similar to Step A by reacting the compound of formula VII with an alkyl 2-cycloalkanonecarboxylate of formula VIII. Said reaction can be conducted at 20°–80° C. in the presence of a suitable acid catalyst such as those mentioned above.

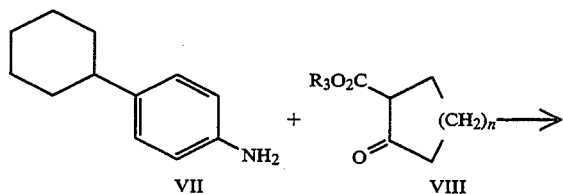

STEP C

A compound of Formula IVa can be prepared by reacting compound IIa with phosphorous pentoxide in the presence of a high boiling tertiary amine such as N,N-dimethylcyclohexylamine. Said reaction can be conducted without additional solvent at a temperature of about 170°–220° C.

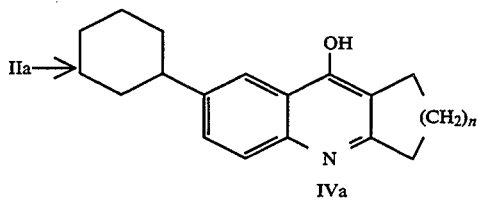

STEP D

Compound IVa can also be prepared by cyclizing compound IIIa at a temperature of 150°–280° C. in a solvent such as liquid paraffin or diphenyl ether.

IIIa→IVa

STEP E

A compounds of Formula IVb can be prepared by reacting compound IVa with phosphorous oxychloride and phosphorous pentachloride. Said reaction can be conducted at a temperature of about 100°–150° C.

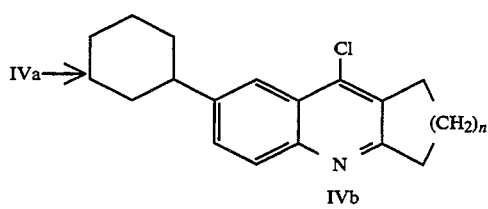

The bromine analogue of compound IIIb can be prepared in a similar manner, namely, for instance by reacting compound IIIa with phosphorus oxybromide and phosphorus pentabromide. The fluorine and iodine analogues of compound IIIa can be prepared by replacing the chlorine atom of compound IIIa with fluorine or iodine in a routine manner known to the art.

STEP F

A compound of Formula IX can be prepared by reacting compound IVb with an amine of formula X. Said reaction can be conducted at a temperature of 120°–220° C. in the presence of an acidic catalyst such as ammonium chloride or phenol.

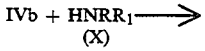
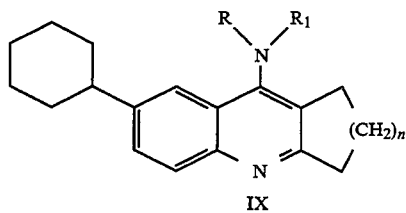

Steps A, C, E and F can be combined into a single step. Thus compound IX can be obtained by heating together a mixture of phosphorous pentoxide, N,N-dimethylcyclohexylamine and the hydrochloride of amine X, and thereafter adding compound Va followed by a cycloalkanone of formula VI. Typically, said reaction is carried out at a temperature of 150°–25° C.

The compounds of Formula I of the present invention can be used for the treatment of various memory dysfunctions characterized by decreased cholinergic function, such as Alzheimer's disease.

This utility can be ascertained by determining the ability of these compounds to inhibit the activity of the enzyme acetylcholinesterase and thereby increase the acetylcholine levels in the brain.

This utility can also be ascertained by determining the ability of these compounds to restore cholinergically deficient memory in the Dark Avoidance Assay. In this assay mice are tested for their ability to remember an unpleasant stimulus for a period of 24 hours. A mouse is placed in a chamber that contains a dark compartment; a strong incandescent light drives it to the dark compartment, where an electric shock is administered through metal plates on the floor. The animal is removed from the testing apparatus and tested again, 24 hours later, for the ability to remember the electric shock.

If scopolamine, an anticholinergic that is known to cause memory impairment, is administered before an animal's initial exposure to the test chamber, the animal re-enters the dark compartment shortly after being placed in the test chamber 24 hours later. This effect of scopolamine is blocked by an active test compound, resulting in a greater interval before re-entry into the dark compartment.

The test results are expressed as the percent of a group of animals in which the effect of scopolamine is blocked, as manifested by an increased interval between being placed in the test chamber and re-entering the dark compartment. Results of Dark Avoidance Assay for some of the compounds of this invention are presented in Table 1 along with a result for a reference compound.

TABLE 1

Dark Avoidance Assay

| Compound | Dose (mg/kg of body weight, s.c) | % of Animals with Scopolamine Induced Memory Deficit Reversal |
| --- | --- | --- |
| 9-amino-7-cyclohexyl-1,2,3,4 tetrahydroacridine hydrochloride | 0.63 | 20% |
| 9-benzylamino-7-dodecyl-1,2,3,4-tetrahydroacridine hydrochloride | 0.63 | 47% |
| 9-amino-6-dodecyl-1,2,3,4-tetrahydroacridine, fumarate (Reference Compound) | 0.16 | 27% |
| Physostigmine | 0.31 | 20% |

Effective quantities of the compounds of the invention may be administered to a patient by any of the various methods, for example, orally as in capsule or tablets, parenterally in the form of sterile solutions or suspensions, and in some cases intravenously in the form of sterile solutions. The free base final products, while effective themselves, may be formulated and administered in the form of their pharmaceutically acceptable acid addition salts for purposes of stability, convenience of crystallization, increased solubility and the like.

Acids useful for preparing the pharmaceutically acceptable acid addition salts of the invention include inorganic acids such as hydrochloric, hydrobromic, sulfuric, nitric, phosphoric and perchloric acids, as well as organic acids such as tartaric, citric, acetic, succinic, maleic, fumaric and oxalic acids.

The active compounds of the present invention may be orally administered, for example, with an inert diluent or with an edible carrier, or they may be enclosed in gelatin capsules, or they may be compressed into tablets. For the purpose of oral therapeutic administration, the active compounds of the invention may be incorporated with excipients and used in the form of tablets, troches, capsules, elixirs, suspensions, syrups, wafers, chewing gum and the like. These preparations should contain at least 0.5% of active compounds, but may be varied depending upon the particular form and may conveniently be between 4% to about 70% of the weight of the unit. The amount of active compound in such compositions is such that a suitable dosage will be obtained. Preferred compositions and preparations according to the present invention are prepared so that an oral dosage unit form contains between 1.0–300 milligrams of active compound.

The tablets, pills, capsules, troches and the like may also contain the following ingredients: a binder such as micro-crystalline cellulose, gum tragacanth or gelatin; an excipient such as starch or lactose, a disintegrating agent such as alginic acid, Primogel, cornstarch and the like; a lubricant such as magnesium stearate or Sterotex; a glidant such as colloidal silicon dioxide; and a sweeting agent such as sucrose or saccharin may be added or a flavoring agent such as peppermint, methyl salicylate, or orange flavoring. When the dosage unit form is a capsule, it may contain, in addition to materials of the above type, a liquid carrier such as a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the active compounds, sucrose as a sweetening agent and certain preservatives, dyes, coloring and flavors. Materials used in preparing these various compositions should be pharmaceutically pure and non-toxic in the amounts used.

For the purpose of parenteral therapeutic administration, the active compounds of the invention may be incorporated into a solution or suspension. These preparations should contain at least 0.1% of active compound, but may be varied between 0.5 and about 30% of the weight thereof. The amount of active compound in such compositions is such that a suitable dosage will be obtained. Preferred compositions and preparations according to the present inventions are prepared so that a parenteral dosage unit contains between 0.5 to 100 milligrams of active compound.

The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparations can be enclosed in disposable syringes or multiple dose vials made of glass or plastic.

Examples of the compounds of this invention include:
9-amino-7-cyclopropyl-1,2,3,4-tetrahydroacridine;
7-cyclopropyl-9-methylamino-1,2,3,4-tetrahydroacridine;
7-cyclopropyl-9-ethylamino-1,2,3,4-tetrahydroacridine;
7-cyclopropyl-9-propylamino-1,2,3,4-tetrahydroacridine;
9-benzylamino-7-cyclopropyl-1,2,3,4-tetrahydroacridine;
7-cyclopropyl-9-(4-fluorobenzylamino)-1,2,3,4-tetrahydroacridine;
9-anilino-7-cyclopropyl-1,2,3,4-tetrahydroacridine;
9-(4-chloroanilino)-7-cyclopropyl-1,2,3,4-tetrahydroacridine;

9-acetamido-7-cyclopropyl-1,2,3,4-tetrahydroacridine;
9-amino-6-cyclopropyl-1,2,3,4-tetrahydroacridine;
6-cyclopropyl-9-methylamino-1,2,3,4-tetrahydroacridine;
9-benzylamino-6-cyclopropyl-1,2,3,4-tetrahydroacridine;
9-anilino-6-cyclopropyl-1,2,3,4-tetrahydroacridine;
9-amino-7-cyclopentyl-1,2,3,4-tetrahydroacridine;
7-cyclopentyl-9-methylamino-1,2,3,4-tetrahydroacridine;
9-benzylamino-7-cyclopentyl-1,2,3,4-tetrahydroacridine;
9-anilino-7-cyclopentyl-1,2,3,4-tetrahydroacridine;
9-amino-7-cyclohexyl-1,2,3,4-tetrahydroacridine;
7-cyclohexyl-9-methylamino-1,2,3,4-tetrahydroacridine;
7-cyclohexyl-9-ethylamino-1,2,3,4-tetrahydroacridine;
7-cyclohexyl-9-propylamino-1,2,3,4-tetrahydroacridine;
9-benzylamino-7-cyclohexyl-1,2,3,4-tetrahydroacridine;
7-cyclohexyl-9-(4-methylbenzylamino)-1,2,3,4-tetrahydroacridine;
9-anilino-7-cyclohexyl-1,2,3,4-tetrahydroacridine;
7-cyclohexyl-9-(4-fluoroanilino)-1,2,3,4-tetrahydroacridine;
9-acetamido-7-cyclohexyl-1,2,3,4-tetrahydroacridine;
9-amino-7-(1,1-dimethylethyl)-1,2,3,4-tetrahydroacridine;
7-(1,1-dimethylethyl)-9-propylamino-1,2,3,4-tetrahydroacridine;
9-butylamino-7-(1,1-dimethylethyl)-1,2,3,4-tetrahydroacridine;
9-benzylamino-7-(1,1-dimethylethyl)-1,2,3,4-tetrahydroacridine;
9-(4-chlorobenzylamino)-7-(1,1-dimethylethyl)-1,2,3,4-tetrahydroacridine;
9-anilino-7-(1,1-dimethylethyl)-1,2,3,4-tetrahydroacridine;
7-(1,1-dimethylethyl)-9-(4-methoxyanilino)-1,2,3,4-tetrahydroacridine;
9-acetamido-7-(1,1-dimethylethyl)-1,2,3,4-tetrahydroacridine;
9-amino-6-(1,1-dimethylethyl)-1,2,3,4-tetrahydroacridine;
6-(1,1-dimethylethyl)-9-propylamino-1,2,3,4-tetrahydroacridine;
9-benzylamino-6-(1,1-dimethylethyl)-1,2,3,4-tetrahydroacridine;
9-anilino-6-(1,1-dimethylethyl)-1,2,3,4-tetrahydroacridine;
9-amino-7-decyl-1,2,3,4-tetrahydroacridine;
9-butylamino-7-decyl-1,2,3,4-tetrahydroacridine;
9-benzylamino-7-decyl-1,2,3,4-tetrahydroacridine;
9-anilino-7-decyl-1,2,3,4-tetrahydroacridine;
9-amino-7-dodecyl-1,2,3,4-tetrahydroacridine;
9-anilino-7-tetradecyl-1,2,3,4-tetrahydroacridine;
9-amino-7-hexadecyl-1,2,3,4-tetrahydroacridine;
9-amino-7-hexadecyl-1,2,3,4-tetrahydroacridine;
9-(4-fluoroanilino)-7-hexadecyl-1,2,3,4-tetrahydroacridine;
9-amino-7-octadecyl-1,2,3,4-tetrahydroacridine;
9-anilino-7-octadecyl-1,2,3,4-tetrahydroacridine;
9-amino-7-cyclopropyl-3,4-dihydro-1H-cyclopenta[b]quinoline;
11-amino-2-cyclopropyl-7,8,9, 10-tetrahydro-6H-cyclohepta[b]quinoline;
9-benzylamino-7-cyclohexyl-1,2,3,4-tetrahydroacridine;
9-benzylamino-7-dodecyl-1,2,3,4-tetrahydroacridine;
9-amino-7-cyclohexyl-1,2,3,4-tetrahydroacridine;
9-amino-7-decyl-1,2,3,4-tetrahydroacridine;
9-benzylamino-7-decyl-1,2,3,4-tetrahydroacridine;
9-amino-7-dodecyl-1,2,3,4-tetrahydroacridine;
7-dodecyl-9-(4-fluorobenzylamino)-1,2,3,4-tetrahydroacridine;
7-cyclohexyl-9-hydroxy-1,2,3,4-tetrahydroacridine;
9-chloro-7-cyclohexyl-1,2,3,4-tetrahydroacridine;
7-dodecyl-9-hydroxy-1,2,3,4-tetrahydroacridine;
9-chloro-7-dodecyl-1,2,3,4-tetrahydroacridine;
7-(1,1-dimethylethyl)-9-hydroxy-1,2,3,4-tetrahydroacridine;
9-benzylamino-7-(2-methylpropyl)-1,2,3,4-tetrahydoracridine;

The following examples are presented in order to illustrate this invention.

EXAMPLE 1

7-Cyclohexyl-9-hydroxy-1,2,3,4-tetrahydroacridine

4-Cyclohexylamine (23.15 g) and 2-ethoxycarbonyl-cyclohexanone (25.0 g) were stirred in 100 mL of benzene containing 0.20 g of p-toluenesulfonic acid monohydrate. After stirring for 4 hours at room temperature the reaction mixture was refluxed for 3 hours with the separation of water. At the end of this time the benzene was evaporated and the residue was dissolved in 150 mL of phenyl ether and the resultant mixture refluxed for 30 minutes. The product which separated upon cooling was filtered off and washed with ether to give 18.22 g of product which was analytically pure without further purification, mp 292°–295° C.

ANALYSIS: Calculated for $C_{19}H_{23}NO$: 81.10% C 8.24% H 4.98% N Found: 80.99% C 8.12% H 4.96% N

EXAMPLE 2

9-Chloro-7-cyclohexyl-1,2,3,4-tetrahydroacridine

7-Cyclohexyl-9-hydroxy-1,2,3,4-tetrahydroacridine (15.539 g) was refluxed for 45 minutes in 100 mL of $POCl_3$. At the end of this time the reaction mixture was concentrated under reduced pressure and the residue was distributed between water and ether. Aqueous ammonia was added portionwise with shaking until all the organic material was dissolved in the ether layer. Evaporation and recrystallization of the residue from methanol gave 14.81 g of analytically pure product, mp 89°–91° C.

ANALYSIS: Calculated for $C_{19}H_{22}ClN$: 76.10% C 7.40% H 4.67% N Found: 76.03% C 7.43% H 4.59% N

EXAMPLE 3

9-Benzylamino-7-cyclohexyl-1,2,3,4-tetrahydroacridine hydrochloride

9-Chloro-7-cyclohexyl-1,2,3,4-tetrahydroacridine (3.0 g) was dissolved in 60 mL of phenol. Benzyl amine (3.21 g) was added and the reaction mixture was heated at 150° C. After 3 hours the reaction mixture was poured into 10% NaOH solution and extracted with ether. The organic phase was washed again with 10% NaOH solution and then with water. Treatment of the organic phase with 5% HCl solution gave a hydrochloride salt which was insoluble in both phases. It was filtered off, recrystallized from isopropanol and dried to give 2.70 g of analytically pure product, mp 272°–274° C.

ANALYSIS: Calculated for $C_{26}H_{30}N_2 \cdot HCl$: 76.72% C 7.68% H 6.88% N Found: 76.92% C 7.72% H 6.84% N

EXAMPLE 4

7-Dodecyl-9-hydroxy-1,2,3,4-tetrahydroacridine

4-Dodecylaniline (15.7 g) was dissolved in 100 mL of benzene and then 2-ethoxycarbonylcyclohexane (10.2 g) was added, followed by 0.20 g of p-toluenesulfonic acid. The reaction mixture was stirred for three days and then refluxed for 2 hours with the separation of H₂O. The benzene was evaporated from this mixture, which was then dissolved in 100 mL of phenyl ether and refluxed for 45 minutes. At the end of this time the reaction mixture was allowed to cool and the precipitated product was filtered off. This crude product was purified by flash chromatography (20% ethyl acetate/$CH_2Cl_2$) and then recrystallized from 1,2-dichloroethane/methanol to give 1.31 g, mp 225°–226°.

ANALYSIS: Calculated for $C_{25}H_{37}NO$: 81.69% C 10.15% H 3.81% N Found: 82.19% C 10.06% H 3.74% N

EXAMPLE 5

9-Chloro-7-dodecyl-1,2,3,4-tetrahydroacridine

Three grams of 7-dodecyl-9-hydroxy-1,2,3,4-tetrahydroacridine was refluxed for 30 minutes in 30 mL of $POCl_3$. At the end of this time the $POCl_3$ was evaporated and the residue distributed between aqueous $NH_3$ and ethyl ether. The organic phase was dried and evaporated to give 9-chloro-7-dodecyl-1,2,3,4-tetrahydroacridine (3.0 g) as a solid. A small sample was recrystallized from methanol to give fine needles, mp 36°–38°.

ANALYSIS: Calculated for $C_{25}H_{36}ClN$: 77.78% C 9.40% H 3.63% N Found: 77.85% C 9.49% H 3.67% N

EXAMPLE 6

9-Benzylamino-7-dodecyl-1,2,3,4-tetrahydroacridine hydrochloride

9-Chloro-7-dodecyl-1,2,3,4-tetrahydroacridine (2.85 g) was heated at 150° in 60 mL of phenol containing 2.46 g of benzylamine. After 3 hours the reaction mixture was distributed between $Et_2O$ and 10% NaOH aqueous solution. The organic phase was washed once more with 10% NaOH, once with H₂O, and then treated with 5% HCl. The insoluble hydrochloride was filtered off and recrystallized from isopropanol to give 2.15 g of analytically pure product, mp 194°–195°.

ANALYSIS: Calculated for $C_{32}H_{44}N_2 \cdot HCl$: 77.93% C 9.20% H 5.68% N Found: 77.77% C 9.60% H 5.97% N

EXAMPLE 7

9-Amino-7-cyclohexyl-1,2,3,4-tetrahydroacridine hydrochloride

Four grams of 9-chloro-7-cyclohexyl-1,2,3,4-tetrahydroacridine was dissolved in 50 ml of phenol and heated to 150° as $NH_3$ was bubbled into the reaction mixture for 2 hours. At the end of this time, the reaction mixture was distributed between $CH_2Cl_2$ and 10% NaOH aqueous solution. The organic phase was washed again with 10% NaOH and then with H₂O. Treatment with 5% HCl solution gave an insoluble hydrochloride which was filtered off and recrystallized from H₂O and then from MeOH-$Et_2O$ to give 2.15 g, mp 320°–325° (d).

ANALYSIS: Calculated for $C_{19}H_{24}N_2 \cdot HCl$: 72.01% C 7.95% H 8.84% N Found: 71.67% C 8.03% H 8.84% N

EXAMPLE 8

9-Amino-6-(1,1-dimethylethyl)-1,2,3,-tetrahydroacridine hydrochloride hydrate 9-Chloro-6-(1,1-dimethylethyl)-1,2,3,4-tetrahydroacridine (4.0 g) was dissolved in 60 ml of phenol and heated at 150° C. for two hours as $NH_3$ was bubbled through the reaction mixture. At the end of this time the solution was distributed between $Et_2O$ and 10% NaOH. The organic phase was then separated and washed with H₂O, after which it was treated with 5% HCl. The insoluble hydrochloride salt was filtered off and recrystallized two times from MeOH/$Et_2O$ to give 2.31 g of product that analyzed correctly as the hydrochloride hydrate.

ANALYSIS: Calculated for $C_{17}H_{22}N_2 \cdot HCl \cdot H_2O$: 66.10% C 8.16% H 9.07% N Found: 66.29% C 8.25% H 9.03% N

EXAMPLE 9

9-Benzylamino-6-(1,1,dimethylethyl)-1,2,3,4-tetrahydroacridine

9-Chloro-6-(1,1-dimethylethyl)-1,2,3,4-tetrahydroacridine (3.0 g) was dissolved in 60 ml of phenol and heated at 150° C. with 3.54 g of benzylamine. After 2 hours the reaction mixture was poured into 10% NaOH and extracted with $Et_2O$. The organic phase was separated, washed with H₂O, and then treated with 5% HCl. The insoluble hydrochloride was filtered off and recrystallized from isopropanol/ether and then from methanol/ether to give 2.09 g of product, m.p. 247° (d).

ANALYSIS: Calculated for $C_{24}H_{28}N_2 \cdot HCl$: 75.66% C 7.67% H 7.36% N Found: 75.61% C 7.78% H 7.27% N

EXAMPLE 10

9-Amino-6-dodecyl-1,2,3,4-tetrahydroacridine, fumarate

9-Chloro-6-dodecyl-1,2,3,4-tetrahydroacridine (2.4 g) was dissolved in 150 ml of phenol. This was heated at 150° C. while ammonia was bubbled into the solution. After 6 hours the reaction mixture was cooled and added to a 10% NaOH solution. The organics were extracted with ethyl acetate (3×) and washed successively with 10% NaOH solution (6×) and water. The organics were dried ($MgSO_4$) and concentrated to give 1.7 g of white solid, m.p. 119°–123° C. This was dissolved in isopropanol and 540 mg of fumaric acid was added. The resulting precipitate was collected and dried to give 2.0 g of white powder, m.p. 213°–216° C.

ANALYSIS: Calculated for $C_{25}H_{38}N_2 \cdot C_4H_4O_4$: 72.16% C 8.77% H 5.80% N Found: 72.06% C 8.84% H 5.85% N

EXAMPLE 11

9-Amino-6-cyclohexyl-1,2,3-tetrahydroacridine, hydrochloride

Ammonia gas was bubbled into a solution of 9-chloro-6-cyclohexyl-1,2,3,4-tetrahydroacridine (3.59 g) in 150 ml of phenol heated at 150° C. Bubbling was continued for 6 hours at which time the reaction mixture was partitioned between dichloromethane and an aqueous NaOH solution. The aqueous phase was extracted with DCM (2×) and the combined organics were treated with 5% HCl solution to give 3.38 g of the hydrochloride salt. This was recrystallized from methanol/ethyl ether to give 2.50 g of white powder, m.p. 332°–336° C. d.

ANALYSIS: Calculated for $C_{19}H_{24}N_2.HCl$: 72.02% C 7.95% H 8.84% N Found: 71.68% C 8.00% H 8.74% N

EXAMPLE 12

9-Benzylamino-6-cyclohexyl-1,2,3,4,-tetrahydroacridine, hydrochloride

A solution of benzylamine (3.2 ml) and 9-chloro-6-cyclohexyl-1,2,3,4-tetrahydroacridine (2.9 g) in 60 ml of phenol was heated at 150° C. for 6 hours The reaction mixture was added to a dilute NaOH solution and extracted with ethyl acetate (2×). The organics were washed with dilute NaOH (2×) and water (1×) and then treated with a 5% HCl solution. This was concentrated to a semi-solid which was triturated with water, filtered and triturated with ethyl ether to give 3.55 g of tan solid, m.p. 262°–270° C. d. This was recrystallized from methanol/ethyl ether to give 2.71 g of off-white solid, m.p. 267°–270° C. d.

ANALYSIS: Calculated for $C_{26}H_{30}N_2.HCl$: 76.73% C 7.68% H 6.88% N Found: 76.65% C 7.80% H 6.84% N

EXAMPLE 13

7-(1,1-Dimethylethyl)-9-hydroxy-1,2,3,4-tetrahydroacridine

A solution prepared from 25.0 g of 4-t-butylaniline-29.0 g of 2-ethoxycarbonylcyclohexanone, 100 ml of benzene and 0.20 g of p-toluenesulfonic acid was refluxed for 6 hours. At the end of this time no more water was collected from the reaction (Dean-Stark trap), so the benzene was evaporated and the residue was dissolved in 80 ml of diphenyl ether. This mixture was refluxed for 1 hour and then allowed to cool to room temperature overnight. The product which had precipitated from this solution was filtered off and washed well with diethyl ether to give 11.52 g of analytically pure product, m.p. 320°–322°.

ANALYSIS: Calculated for $C_{17}H_{21}NO$: 79.96% C 8.29% H 5.49% N Found: 80.18% C 8.28% H 5.40% N

EXAMPLE 14

9-Amino-7-(1,1-dimethyl)-1,2,3,4-tetrahydroacridine, hydrochloride 7-(1,1-Dimethylethyl)-9-hydroxy-1,2,3,4-tetrahydroacridine was refluxed in $POCl_3$ and worked up by evaporating the $POCl_3$ and distributing the residue between $Et_2O$ and aqueous $NH_3$. The 9-chloro product obtained by drying and concentrating the organic phase was used without further purification. A 4.0 g sample of 9-Chloro-7-(1,1-dimethylethyl)-1,2,3,4-tetrahydroacridine maintained at 150° C while $NH_3$ was bubbled into the solution. After 2 hours the reaction mixture was distributed between 10% NaOH and 2-butanone and then the organic phase was dried and concentrated. The residue was dissolved in $Et_2O$ and treated with 5% HCl, giving an insoluble hydrochloride which was filtered off and recrystallized from $MeOH/Et_2O$ to give 3.11 g of analytically pure product, m.p. 325° C. d.

ANALYSIS: Calculated for $C_{17}H_{22}N_2.HCl$: 70.20% C 7.97% H 9.63% N Found: 70.46% C 8.02% H 9.70% N

EXAMPLE 15

9-Benzylamino-7-(1,1-dimethylethyl)-1,2,3,4-tetrahydroacridine, hydrochloride 7-(1,1-Dimethylethyl)-9-hydroxy-1,2,3,4-tetrahydroacridine (9.46 g) was refluxed for 30 minutes in 50 ml of $POCl_3$. The volatiles were evaporated and the residue was distributed between aqueous $NH_3$ and $Et_2O$. Concentration of the organic phase gave 8.24 g of 9-chloro-7-1,1-dimethylethyl)-1,2,3,4-tetrahydroacridine.

A 3.0 g portion of the above chloro compound was dissolved in 60 ml of phenol to which benzylamine (3.54 g) was then added. This reaction mixture was heated at 150° C. for 3 hours and then allowed to cool. It was distributed between 10% NaOH and water. Treatment of the organic phase with 5% HCl solution gave an insoluble hydrochloride which was filtered off and recrystallized from $MeOH/Et_2O$ to give 2.16 g of analytically product, m.p. 285° d.

ANALYSIS: Calculated for $C_{24}H_{28}N_2.HCl$: 75.67% C 7.67% H 7.36% N Found: 75.94% C 7.73% H 7.39% N

EXAMPLE 16

9-Amino-7-decyl-S1,2,3,4-tetrahydroacridine, hydrochloride.

9-Chloro-7-decyl-1,2,3,4-tetrahydroacridine (4.50 g) was dissolved in 50 ml of phenol and the reaction mixture heated to 150° C. as $NH_3$ was bubled into the solution. After 2 hours the reaction mixture was distributed between $Et_2O$ and 10% NaOH and then the organic phase was separated and treated with 5% HCl. The insoluble hydrochloride was filtered off and recrystallized from $EtOAc/EtOH$ to give 2.51 g, m.p. 240°–242° C.

ANALYSIS: Calculated for $C_{23}H_{34}N_2.HCl$: 73.66% C 9.41% H 7.47% N Found: 73.47% C 9.51% H 7.46% N

EXAMPLE 17

9-Benzylamino-7-decyl-1,2,3,4-tetrahydroacridine hydrochloride

9-Chloro-7-decyl-1,2,3,4-tetrahydroacridine hydrochloride (5.0 g) was dissolved in 50 ml of phenol and heated at 150° C. with 3.50 g of benzylamine. After 2 hours at this temperature the reaction mixture was poured into 10% NaOH and extracted with $Et_2O$. The organic phase was separated, washed with water and treated with 5% HCl. The insoluble hydrochloride was filtered off and recrystallized from $MeOH/Et_2O$ to give 2.59 g of product, m.p. 215° C.

ANALYSIS: Calculated for $C_{30}H_{40}N_2.HCl$: 77.47% C 8.89% H 6.02% N Found: 77.54% C 9.01% H 6.06% N

EXAMPLE 18

9-Amino-7-dodecyl-1,2,3,4-tetrahydroacridine, hydrochloride

7-Dodecyl-9-hydroxy-1,2,3,4-tetrahydroacridine was refluxed in $POCl_3$ and worked up by evaporating the $POCl_3$ and distributing the residue between $Et_2O$ and aqueous $NH_3$. The 9-chloro product obtained by drying and concentrating the organic phase was used without further purification.

A 4.0 g sample of 9-Chloro-7-dodecyl-1,2,3,4-tetrahydroacridine was heated at 150° C. as $NH_3$ was bubbled into the solution. After 2 hours the reaction mixture was distributed between 10% NaOH and 2-butanone and then the organic phase was dried and concentrated. The residue was dissolved in $Et_2O$ and treated with 5% HCl. The insoluble hydrochloride was filtered off and recrystallized from $MeOH/Et_2O$ to give 2.32 g of analytically pure product, m.p. 257° d.

ANALYSIS: Calculated for $C_{25}H_{38}N_2 \cdot HCl$: 74.50% C 9.75% H 6.95% N Found: 74.85% C 9.86% H 6.99% N

EXAMPLE 19

7-Dodecyl-9-(4-fluorobenzylamino)-1,2,3,4-tetrahydroacridine, hydrochloride

9-Chloro-7-dodecyl-1,2,3,4-tetrahydroacridine (3.55 g) was dissolved in 60 ml of phenol, 4-fluorobenzylamine was added (3.75 g) and the reaction mixture was heated to 150° C. After 2 hours the reaction mixture was poured into 10 % NaOH and extracted with $Et_2O$. The organic phase was separated, washed with $H_2O$, and then treated with 5% HCl. The insoluble hydrochloride was filtered and recrystallized from $EtOH/Et_2O$ to give 2.375 g, m.p. 208°-210° C.

ANALYSIS: Calculated for $C_{32}H_{43}FN_2 \cdot HCl$: 75.19% C 8.68% H 5.48% N Found: 75.51% C 8.70% H 5.32% N

We claim:

1. A compound having the formula

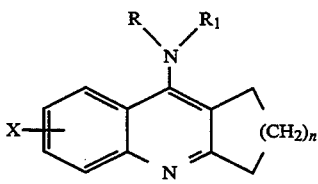

wherein n is an integer of 1 to 4;

X is alkyl of 6-18 carbon atoms, cycloalkyl of 3-7 carbon atoms or cycloalkylloweralkyl;

R is hydrogen, loweralkyl or loweralkylcarbonyl; and $R_1$ is hydrogen, loweralkyl, loweralkylcarbonyl, aryl, diarylloweralkyl, diloweralkylaminoloweralkyl, arylloweralkyl, diarylloweralkyl, aryl($CH_2$-)$_m$—O—($CH_2$)$_l$ or diarylCH($CH_2$)$_k$—O—($CH_2$-)$_l$—;

the term aryl in each occurrence signifying a phenyl group optionally substituted with 1, 2 or 3 substituents each of which being independently loweralkyl, loweralkoxy, halogen, hydroxy, trifluoromethyl, phenoxy or benzyloxy, m is an integer of 0 to 4. k is an integer of 0 to 3, and l is an integer of 2, 3, 4 or 5 where the sum of m+l is $\leq 6$ and the sum of k+l is $\leq 5$; a stereo, optical or geometrical isomer thereof, or a pharmaceutically acceptable acid addition salt thereof.

2. The compound as defined in claim 1 where R is hydrogen and $R_1$ is hydrogen or arylloweralkyl.

3. The compound as defined in claim 1, where n is 2.

4. The compound as defined in claim 2, where n is 2.

5. The compound as defined in claim 1 which is 9-amino-7-cyclopropyl-1,2,3,4-tetrahydroacridine.

6. The compound as defined in claim 1 which is 7-cyclopropyl-9-methylamino-1,2,3,4-tetrahydroacridine.

7. The compound as defined in claim 1 which is 7-cyclopropyl-9-methylamino-1,2,3,4-tetrahydroacridine.

8. The compound as defined in claim 1 which is 7-cyclopropyl-9-propylamino-1,2,3,4-tetrahydroacridine.

9. The compound as defined in claim 1 which is 9-benzylamino-7-cyclopropyl-1,2,3,4-tetrahydroacridine.

10. The compound as defined in claim 1 which is 7-cyclopropyl-9-(4-fluorobenzylamino)-1,2,3,4-tetrahydroacridine.

11. The compound as defined in claim 1 which is 9-anilino-7-cyclopropyl-1,2,3,4-tetrahydroacridine.

12. The compound as defined in claim 1 which is 9-(4-chloroanilino)-7-cyclopropyl-1,2,3,4-tetrahydroacridine.

13. The compound as defined in claim 1 which is 9-acetamido-7-cyclopropyl-1,2,3,4-tetrahydroacridine.

14. The compound as defined in claim 1 which is 9-amino-6-cyclopropyl-1,2,3,4-tetrahydroacridine.

15. The compound as defined in claim 1 which is 6-cyclopropyl-9-methylamino-1,2,3,4-tetrahydroacridine.

16. The compound as defined in claim 1 which is 9-benzylamino-6-cyclopropyl-1,2,3,4-tetrahydroacridine.

17. The compound as defined in claim 1 which is 9-anilino-6-cyclopropyl-1,2,3,4-tetrahydroacridine.

18. The compound as defined in claim 1 which is 9-amino-7-cyclopentyl-1,2,3,4-tetrahydroacridine.

19. The compound as defined in claim 1 which is 7-cyclopentyl-9-methylamino-1,2,3,4-tetrahydroacridine.

20. The compound as defined in claim 1 which is 9-benzylamino-7-cyclopentyl-1,2,3,4-tetrahydroacridine.

21. The compound as defined in claim 1 which is 9-anilino-7-cyclopentyl-1,2,3,4-tetrahydroacridine.

22. The compound as defined in claim 1 which is 9-amino-7-cyclohexyl-1,2,3,4-tetrahydroacridine.

23. The compound as defined in claim 1 which is 7-cyclohexyl-9-methylamino-1,2,3,4-tetrahydroacridine.

24. The compound as defined in claim 1 which is 7-cyclohexyl-9-ethylamino-1,2,3,4-tetrahydroacridine.

25. The compound as defined in claim 1 which is 7-cyclohexyl-9-propylamino-1,2,3,4-tetrahydroacridine.

26. The compound as defined in claim 1 which is 9-benzylamino-7-cyclohexyl-1,2,3,4-tetrahydroacridine.

27. The compound as defined in claim 1 which is 7-cyclohexyl-9-(4-methylbenzylamino)-1,2,3,4-tetrahydroacridine.

28. The compound as defined in claim 1 which is 9-anilino-7-cyclohexyl-1,2,3,4-tetrahydroacridine.

29. The compound as defined in claim 1 which is 7-cyclohexyl-9-(4-fluoroanilino)-1,2,3,4-tetrahydroacrine.

30. The compound as defined in claim 1 which is 9-acetamido-7-cyclohexyl-1,2,3,4-tetrahydroacridine.

31. The compound as defined in claim 1 which is 9-amino-7-decyl-1,2,3,4-tetrahydroacridine.

32. The compound as defined in claim 1 which is 9-butylamino-7-decyl-1,2,3,4-tetrahydroacridine.

33. The compound as defined in claim 1 which is 9-benzylamino-7-decyl-1,2,3,4-tetrahydroacridine.

34. The compound as defined in claim 1 which is 9-anilino-7-decyl-1,2,3,4-tetrahydroacridine.

35. The compound as defined in claim 1 which is 9-amino-7-dodecyl-1,2,3,4-tetrahydroacridine.

36. The compound as defined in claim 1 which is 9-anilino-7-tetradecyl-1,2,3,-tetrahydroacridine.

37. The compound as defined in claim 1 which is 9-amino-7-hexadecyl-1,2,3,4-tetrahydroacridine.

38. The compound as defined in claim 1 which is 9-(4-fluoroanilino)-7-hexadecyl-1,2,3,4-tetrahydroacridine.

39. The compound as defined in claim 1 which is 9-amino-7-octadecyl-1,2,3,4-tetrahydroacridine.

40. The compound as defined in claim 1 which is 9-anilino-7-octadecyl-1,2,3,4-tetrahydroacridine.

41. The compound as defined in claim 1 which is 9-amino-7-cyclopropyl-3,4-dihydro-1H-cyclopenta[b]quinoline.

42. The compound as defined in claim 1 which is 11-amino-2-cyclopropyl-7,8,9,10-tetrahydro-6H-cyclohepto[b]quinoline.

43. The compound as defined in claim 1 which is 9-benzylamino-6-cyclohexyl-1,2,3,4-tetrahydroacridine.

44. The compound as defined in claim 1 which is 9-benzylamino-7-dodecyl-1,2,3,4-tetrahydroacridine.

45. The compound as defined in claim 1 which is 9-amino-6-cyclohexyl-1,2,3,4-tetrahydroacridine.

46. The compound as defined in claim 1 which is 9-amino-7-decyl-1,2,3,4-tetrahydroacridine.

47. The compound as defined in claim 1 which is 9-benzylamino-7-decyl-1,2,3,4-tetrahydroacridine.

48. The compound as defined in claim 1 which is 9-amino-6-dodecyl-1,2,3,4-tetrahydroacridine.

49. The compound as defined in claim 1 which is 7-dodecyl-9-(4-fluorobenzylamino)-1,2,3,4-tetrahydroacridine.

50. A compound having the formula

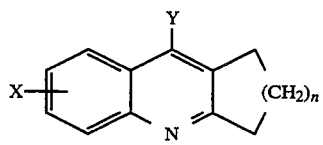

wherein n is an integer of 1 to 4; X is alkyl of 6–18 carbon atoms, cycloalkyl of 3–7 carbon atoms or cycloalkylloweralkyl; and Y is halogen, hydroxy or loweralkoxy.

51. The compound as defined in claim 50, where n is 2.

52. The compound as defined in claim 50 which is 7-cyclohexyl-9-hydroxy-1,2,3,4-tetrahydroacridine.

53. The compound as defined in claim 50 which is 9-chloro-7-cyclohexyl-1,2,3,4-tetrahydroacridine.

54. The compound as defined in claim 50 which is 7-dodecyl-9-hydroxy-1,2,3,4-tetrahydroacridine.

55. The compound as defined in claim 50 which is 9-chloro-7-dodecyl-1,2,3,4-tetrahydroacridine.

56. A pharmaceutical composition for increasing the cholinergic function in a mammal which comprises an effective amount of a compound as defined in claim 1 and a carrier therefor, 57. The pharmaceutical composition as defined in claim 56 which comprises 9-amino-7-cyclopropyl-1,2,3,4-tetrahydroacridine.

58. The pharmaceutical composition as defined in claim 56 which comprises 7-cyclohexyl-9-methylamino-1,2,3,4-tetrahydroacridine.

59. The pharmaceutical composition as defined in claim 56 which comprises 9-anilino-7-decyl-1,2,3,4-tetrahydroacridine.

60. The pharmaceutical composition as defined in claim 56 which comprises 9-amino-6-cyclohexyl-1,2,3,4-tetrahydroacridine.

61. A method of increasing the cholinergic function in a mammal which comprises administering to the mammal an effective cholinergic function increasing amount of a compound as defined in claim 1.

62. The method as defined in claim 61 which comprises the administration of 9-amino-7-cyclopropyl-2,3,4-tetrahydroacridine.

63. The method as defined in claim 61 which comprises the administration of 7-cyclohexyl-9-methylamino-1,2,3,4-tetrahydroacridine.

64. The method as defined in claim 61 which comprises the administration of 9-anilino-7-decyl-1,2,3,4-tetrahydroacridine.

65. The method as defined in claim 61 which comprises the administration of 9-amino-6-cyclohexyl-1,2,3,4-tetrahydroacridine.

* * * * *